US00PP14152P29

(12) United States Plant Patent
van Gaalen

(10) Patent No.: US PP14,152 P2
(45) Date of Patent: Sep. 16, 2003

(54) DELPHINIUM PLANT NAMED 'DELGA STAM'

(76) Inventor: Iranaeus Antonius Maria van Gaalen, Noordhoornseweg 37, 2635 GC Den Hoorn (NL)

( * ) Notice: Subject to any disclaimer, the term of this patent is extended or adjusted under 35 U.S.C. 154(b) by 0 days.

(21) Appl. No.: 10/247,554

(22) Filed: Sep. 20, 2002

(51) Int. Cl.[7] ..... A01H 5/00
(52) U.S. Cl. ..... Plt./263

(58) Field of Search ..... Plt./263

*Primary Examiner*—Kent Bell
(74) *Attorney, Agent, or Firm*—Foley & Lardner

(57) ABSTRACT

A new and distinct cultivar of Delphinium plant named 'Delga Stam', as described and illustrated, and particularly characterized by green leaf color, violet blue/greyed-green flower color, upward facing flowers, new flowers grow from the center of existing flower after 4–8 weeks, flowers are persistent without adding pretreatment, much higher stem production per plant.

2 Drawing Sheets

Latin name of the genus and species of the plant claimed: Delphinium hybrid.
Variety denomination: 'Delga Stam'.

BACKGROUND OF THE INVENTION

The present invention comprises a new and distinct cultivar of Delphinium, botanically known as Delphinium hybrid and hereinafter referred to by the cultivar name 'Delga Stam'.

The new Delphinium was discovered by the inventor, Irenaeus A. M. van Gaalen, in Den Hoorn, The Netherlands, in May 2001 as a plant within the progeny from the cross between *Delphinium belladona* 'Völkerfrieden' (female, unpatented) and Delphinium L. 'Peacemaker' (male, unpatented).

Asexual propagation of the new cultivar by vegetative cuttings cuttings taken at Den Hoorn, The Netherlands, has shown that the unique features of this new Delphinium are stable and reproduce true to type in successive generations.

BRIEF DESCRIPTION OF THE INVENTION

Plants of the cultivar 'Delga Stam' have not been observed under all possible environmental conditions. The phenotype may vary somewhat with variations in the environment such as temperature, light intensity, day length, and fertility level without, however, any variance in genotype.

The following observations, measurements and values describe the new cultivar as grown in Den Hoorn, The Netherlands in a normal glass greenhouse under average day temperatures between 18 to 32 degrees Celsius and 10 to 18 degrees Celsius at night. No artificial lighting, photoperiodic treatments or other cultural or environmental treatments are conducted, no growth retardants are added. The plant described was one year old and field grown under glasshouse structure.

The following traits have been repeatedly observed and are determined to be the unique characteristics of 'Delga Stam'. These characteristics in combination distinguish 'Delga Stam' as a new and distinct cultivar:

1. green leaf color;
2. violet blue/greyed-green flower color;

3. upward facing flowers;
4: new flowers grow from the center of existing flower after 4–8 weeks;
5. flowers are persistent without adding pretreatment; and
6. much higher stem production per plant.

Compared to 'Völkerfrieden', 'Delga Stam' has upward facing flowers whereas 'Volkerfrieden' has horizontally facing flowers. The flower color of 'Delga Stam' is violet-blue with greyed-green whereas the flower color of 'Volkerfrieden' is blue. New flowers of 'Delga Stam' grow continuously from the center of existing flowers after 4–8 weeks with sufficient light and temperature; 'Volkerfrieden' does not do this. The flowers of 'Delga Stam' are persistent unlike the flowers of 'Volkerfrieden'. Volkerfrieden needs pretreatment after cutting to avoid early flower drop, 'Delga Stam' does not need pretreatment. 'Delga Stam' has a much higher temperature resistance than 'Volkerfrieden'. 'Delga Stam' produces significantly more stems than 'Volkerfrieden'.

Compared to *Delphinium belladonna* 'Peacemaker', the sepals of 'Delga Stam' are violet blue with a broad greyed-green lateral band in the center whereas 'Peacemaker' has violet-blue sepals. The sepal shape of 'Delga stam' is elliptic whereas the sepal shape of 'Peacemaker' is obovate. 'Delga Stam' has upward facing flowers whereas 'Peacemaker' has horizontally facing flowers. New flowers of 'Delga Stam' grow from the center of existing flowers after 4–8 weeks with sufficient light and temperature; 'Peacemaker' does not do this. The flowers of 'Delga Stam' are persistent unlike the flowers of 'Peacemaker'. 'Peacemaker' needs pretreatment after cutting to avoid early flower drop, 'Delga Stam' does not need pretreatment.

BRIEF DESCRIPTION OF THE DRAWINGS

The accompanying photographic drawings shows typical flower and foliage characteristics of 'Delga Stam' with colors being as true as possible with illustrations of this type. The drawing on the left side of the first sheet shows a plant with mature flowers grown in a green house. The drawing on the right side of the first sheet shows a close-up of flowers between immature and mature stage. The drawing on the left side of the second sheet shows a comparison between 'Volkerfrieden' (left) and 'Delga Stam' (right). The drawing on the top middle of the second sheet shows a close-up of an immature flower. The drawing on the top right of the second sheet shows a close-up of an immature flower. The drawing on the bottom right of the second sheet show a close-up of a mature flower.

DETAILED BOTANICAL DESCRIPTION

The following measurements were taken in Den Hoorn, The Netherlands, on May 27, 2002, 12 months after planting of rooted cuttings into 9 inch pots. The plants had not been pinched.

In the following description color references are made to The Royal Horticultural Society Colour Chart (R.H.S.). The color values were determined indoors from flowers developed in a greenhouse in May 2002, in Den Hoorn, The Netherlands.

Plant description:

*Type.*—Herbacaeos perennial.
*Crop time.*—20 weeks from rooted cutting.
*Shape.*—Narrow triangular.
*Branching habit.*—Heavily branched; main (flowering) shoots appear from base, no lateral shoots. No lateral branches; average number of main stems: 15.
*Rooting habit.*—Freely branching.
*Plant height.*—Average 85 cm.
*Area of spread.*—Average 55 cm.
*Vigor.*—Moderate, 30–40 cm per month.
*Growth rate.*—Moderate, 30–40 cm per month.
*Growth habit.*—Upright.
*High temperature tolerance.*—At least tolerant to temperatures up to 35° C.
*Low temperature tolerance.*—At least hardy to USDA Zone 7.

Stem:

*Internode length.*—Average 7.5 cm (main stems).
*Color.*—Green,RHS 143A.
*Stem appearance/shape.*—Smooth, not very glossy, no pubescence.
*Stem aspect.*—Circular to somewhat flattened.
*Stem strength.*—Strong.
*Stem length.*—Average main stem length 85 cm.
*Stem diameter.*—Average main stem diameter 6 mm.
*Number of harvestable stems per year.*—Average 30.

Peduncle:

*Length.*—Average 38 cm.
*Diameter.*—Average 3 mm.
*Angle.*—0° to 10° (straight on top of branch=0°).
*Strength.*—Strong.
*Color.*—Green, RHS 143B.

Foliage description:

*Arrangement.*—Alternate.
*Compound or single.*—Single.
*Quantity per flower stem.*—Main branches: average 15.
*Length.*—Average 11.2 cm.
*Width.*—Average 15.5 cm.
*Aspect.*—Flat.
*Shape.*—Pedately cleft to very deep pedately lobed.
*Apex.*—Acute.
*Base.*—Attenuate.
*Margin.*—Incised to laciniate.
*Texture.*—Smooth, dull, no leaf pubescence.
*Immature leaf color.*—Color of upper surface: Green, RHS 137A. Color of lower surface: Green, RHS 138B.
*Mature leaf color.*—Color of upper surface: Green, RHS 139A. Color of lower surface: Green; RHS N138B to N138C.
*Venation.*—Laciniate.
*Petiole length.*—Average 15 cm, basal leaf petiole longer, average 26 cm.
*Petiole diameter.*—Average 2 mm.
*Petiole color.*—Green, RHS 143B.
*Vein color upper side.*—Green, RHS 143A to 143B.
*Vein color under side.*—Green, RHS 143B.

Flower description:

*Inflorescence type/form.*—Raceme.
*Inflorescence height.*—Average 40 cm.
*Inflorescence diameter.*—Average 25 cm.
*Flower arrangement.*—Terminal raceme.
*Flower type.*—Single.
*Flower aspect.*—Upright.
*Natural flowering season.*—Summer, June–August.
*Flower longevity.*—Average 6.5 weeks on plant, average 17 days as cut flower.
*Quantity.*—Average 300 per plant, average 20 per lateral stem.
*Fragrance.*—None.
*Flowering habit.*—Once a year, continuously.
*Time to flower.*—Approximately 9 months.
*Other characteristics.*—On both sides of each pedicel is one bract (alternate); length 3.7 cm, linear shaped, acute tip, green in color: upper side RHS 139A, lower side RHS 138A.

From the center of each flower grows a "pedicel" straight and upright (angle: 0°), average length 1.9 cm, average width 1.5 mm, green in color RHS 137C, densely covered with very short light green hairs; on top of this pedicel are 3 (three) "leaves" with their margins fused, thus creating a closed, tubular leaf; shaped narrow oblanceolate; top aristate; average length 3.9 cm, average width 4 mm; green in color RHS 137C (both surfaces), densely covered with very short light green hairs; only the under side of these leaves is visible, because the margins are fused, the upper side is inside the "tube".

Buds:

*Length.*—Average 1 cm, diameter is 7 mm.
*Spur length.*—Average 5 mm.
*Shape.*—Obovate.
*Color.*—Green RHS 143A, base lighter RHS 143C.
*Quantity.*—Average 20.
*Flower size.*—Average 6.5 cm in depth (including spur), average 5 cm in diameter.
*Flower appearance.*—Zygomorphic.
*Rate of flower opening.*—Approximately 20% of the flowers are opened at one stage; flowering period is about 2.5 months.

Petals:

*Arrangement.*—Zygomorphic, placed above ovary.
*Quantity.*—4 (rarely 5), not fused.
*Appearance.*—Dull.
*Texture.*—Smooth, lower petals with hairs in the centers.
*Shape.*—Lower petals spathulate to flabellate, upper petals narrow spathulate to almost oblong.
*Margin.*—Entire.
*Length.*—Lower petals average 1.4 cm, upper petals average 1.3 cm.

*Width.*—Lower petals average 7 mm, upper petals average 3.5 mm.

*Tip.*—Lower petals retused, upper petals obtuse.

*Upper surface color when opening.*—Lower petals violet-blue, RHS 90B to 90C, center greyed-green RHS 189A with lighter (RHS 189C) hairs; upper petals violet-blue RHS 94A.

*Lower surface color.*—Lower petals violet-blue RHS 90C to 90D, center greyed-green RHS 189A, upper petals violet-blue RHS 93A.

*Upper surface color fully opened.*—Lower petals violet-blue; RHS 90B to 90C, center greyed-green RHS 189A with lighter (RHS 189C) hairs; upper petals violet-blue RHS 94A.

*Lower surface color fully opened.*—Lower petals violet-blue RHS 90C to 90D, center greyed-green RHS 189A; upper petals violet-blue RHS 93A; petal color does not fade, there are no petaloids.

Sepals:

*Quantity.*—5.

*Appearance.*—Smooth, dull.

*Arrangement.*—Rotate, zygomorphic.

*Shape.*—Elliptic (only rarely obovate).

*Length.*—Average 4.6 cm.

*Diameter.*—Average 1.8 cm.

*Texture.*—Smooth, dull.

*Margin.*—Entire.

*Color immature upper side.*—Green, darker than but closest to RHS 139A, with violet-blue margins RHS 98B.

*Color immature under side.*—Green RHS 137C with violet-blue margins RHS 98B.

*Color mature upper side.*—Green, darker than but closest to RHS 139A, with violet-blue margins RHS 98B.

*Color mature under side.*—Green; RHS 137C with violet-blue margins RHS 98B.

*Sepal apex.*—Acute.

*Sepal base.*—Narrow cuneate, but upper sepal ending in a spur; average length of spur 8 mm.

Pedicels:

*Length.*—Average 20.5 cm.

*Width.*—1.5 mm.

*Angle.*—10° to 450° (0°=straight on top of peduncle).

*Strength.*—Strong.

*Color.*—Green RHS 141A to 141B.

Reproductive organs:

*Stamens.*—Number of stamens: Average 30.

*Anthers.*—Anther shape: Basifixed, kidney-shaped. Anther size: Average 1.5 mm. Anther color: Greyed-green RHS 197A. Pollen: Amount: Very low. Color: Green-white; approximately RHS 157A.

*Pistils.*—None.

*Stigma.*—None.

*Calyx.*—Calyx shape: Rotate, slightly cup-shaped. Calyx length: Average 2.5 cm (excluding spur). Calyx diameter: Average 5 cm.

*Ovary color.*—Yellow-green; RHS 144D.

*Seed.*—None.

*Pest/disease resistance/susceptibility.*—Not more susceptible to pests and diseases than other Delphinium varieties.

I claim:

1. A new and distinct cultivar of Delphinium plant named 'Delga Stam', as described and illustrated.

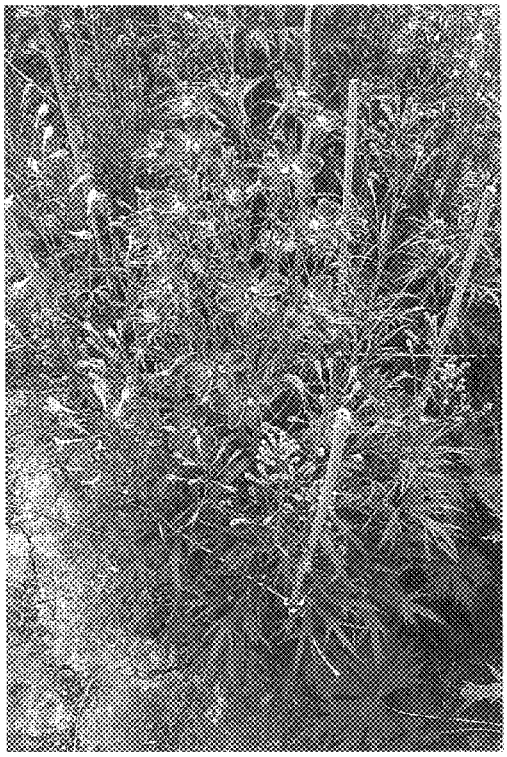
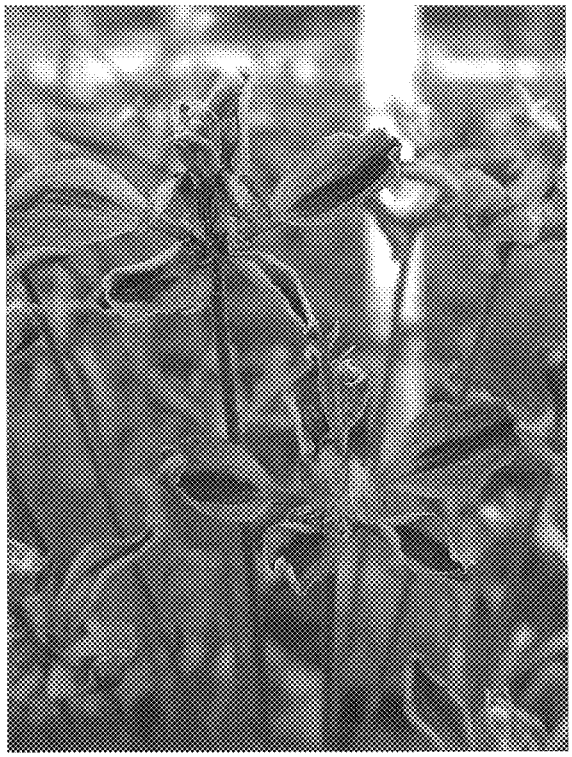

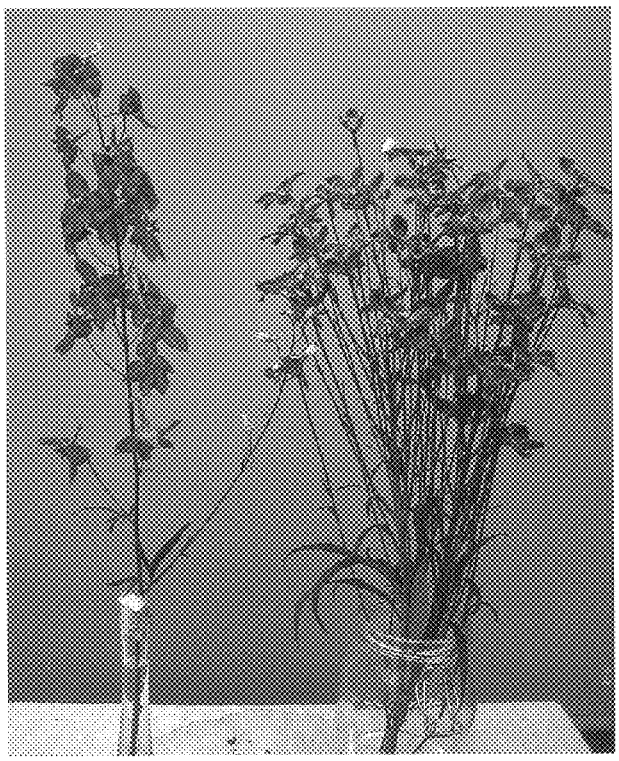
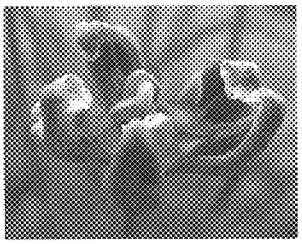
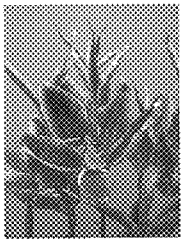
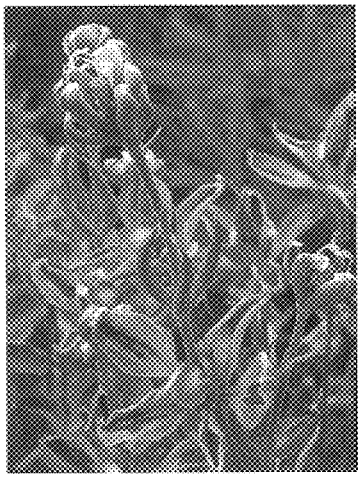

* * * * *